United States Patent [19]

Augsburger

[11] Patent Number: 5,645,548

[45] Date of Patent: Jul. 8, 1997

[54] OSTEOTOMY FRAME

[76] Inventor: Samuel F. Augsburger, 2409 Woodruff Way, Lexington, Ky. 40515

[21] Appl. No.: 601,797

[22] Filed: Feb. 15, 1996

[51] Int. Cl.⁶ .................................................. A61B 17/56
[52] U.S. Cl. .................................................. 606/87; 606/54
[58] Field of Search .................................... 606/54, 55, 56, 606/57, 58, 59, 86, 87, 88

[56] References Cited

U.S. PATENT DOCUMENTS

| | | | |
|---|---|---|---|
| 4,335,715 | 6/1982 | Kirkley | 128/92 |
| 4,628,922 | 12/1986 | Dewar | 128/92 Z |
| 4,747,400 | 5/1988 | Koeneman et al. | 128/92 |
| 5,074,866 | 12/1991 | Sherman et al. | 606/56 |
| 5,275,599 | 1/1994 | Zbikowski et al. | 606/54 |
| 5,358,504 | 10/1994 | Paley et al. | 606/56 |
| 5,372,597 | 12/1994 | Hotchkiss et al. | 606/56 |
| 5,397,322 | 3/1995 | Campopiano | 606/57 |
| 5,437,667 | 8/1995 | Papierski et al. | 606/55 |

FOREIGN PATENT DOCUMENTS

| | | |
|---|---|---|
| 3411286 | 1/1986 | Germany . |
| 880416 | 11/1981 | U.S.S.R. . |

*Primary Examiner*—Michael Buiz
*Assistant Examiner*—David O. Reip
*Attorney, Agent, or Firm*—Bielen, Peterson & Lampe

[57] ABSTRACT

An osteotomy frame for aligning first and second bone portions utilizing a pair of clamps intended for holding bone portions that have been created by use of a bone saw guide. An arm is connected to the first clamp and is pivoted relative to an axis. A scale interacts with the arm to indicate a value of rotation of the first bone portion about the axis, while being held by the first clamp.

13 Claims, 4 Drawing Sheets

OSTEOTOMY FRAME

BACKGROUND OF THE INVENTION

The present invention relates to a novel and useful osteotomy frame.

Osteotomies involve a cutting, rotating, and refixation of a pair of boney parts utilizing plates, screws, pins, and the like. Such surgical procedures are undertaken in order to correct a misalignment at an anatomical joint, such as a knee. The rotating step in an osteotomy involves rotating one boney part with respect to the other boney part after cutting of a unitary boney part by a bone saw guide. In certain cases, such rotation takes place about one or two axes and must be accurately performed.

In the past, devices have been proposed for aligning bones to correct deformities and fractures. For example, U.S. Pat. No. 5,074,866 shows a fixation frame to stretch or compress the bone using the Llizarov method.

U.S. Pat. No. 5,372,597, describes a supination-pronation device for treating and preventing injuries to elbow joints and radial head fractures. Pins which screw into bone fragments are employed in this device.

U.S. Pat. Nos. 4,628,922; 4,747,400; 5,275,599; and 5,397,322 show fracture reduction apparatuses for fixing fractures into place in order to accomplish healing of the same.

In the past, after a bone has been cut in an osteotomy procedure, rotation, according to a pre-calculated degree, has taken place manually. Usually two persons are involved, one to rotate and hold the boney parts, and the other to fixate. Other devices have been proposed to more accurately perform an osteotomy. For example, U.S. Pat. No. 4,335,715 uses a pair of pins that are drilled into the bone portions and rotated along an arcuate scale relative to one another. USSR patent 0880416 shows a bone saw guide and clamping device which also permits rotation of a boney part along an arcuate path.

U.S. Pat. No. 5,358,504 is employed to correct bone deformities by rotating one boney part relative to another along an axis which is generally perpendicular to the axis of the bone.

An osteotomy frame which permits the accurate rotation of one boney party relative to another eccentric to the center of rotation of the bone would be a notable advance in the medical arts.

SUMMARY OF THE INVENTION

In accordance with the present invention, a novel and useful osteotomy frame is herein provided.

The osteotomy frame of the present invention is employed with an osteotomy surgical procedure in which a bone is cut using a bone saw. The frame of the present invention employs a first clamp which is intended for holding a first bone portion and a second clamp for holding the second bone portion. Each of the clamps are capable of exerting a varying degree of pressure around the particular bone portion, and each includes an arm which extends outwardly from the particular bone portion.

The arm of the first clamp is rotated about the axis of the first boney part by pivoting means. Such pivoting means may take the form of an arcuate member having a track and a movable structure or glide plate capable of riding on said track. The arm is connected to the movable structure. In certain embodiments, the arcuate may be formed with a plurality of tracks and the movable structure may include a cam or cams to ride in the track of the arcuate member. In this regard, the arcuate member track may be an arcuate groove or slot.

Stop means may also be employed for fixing the rotation of the arm relative to the axis of the bone. Such stop means may include the provision of a plurality of openings spaced a predetermined distance from each other on the arcuate member. A protuberance which engages the movable structure would also be capable of entering any of the plurality of openings on the arcuate member to arrest movement between the movable structure and the arcuate member. In this way, the rotation of the bone connected to the first clamp is also prevented from moving once the stop means is employed.

Moreover, the rotation of the first arm connected to the first clamp by the pivoting means is indicated by a scale. The scale may be placed on a surface of the arcuate member, and, in certain cases, may be related to the plurality of openings found on the arcuate member for engagement by the protuberance of the stop means. Thus, the rotation of the first bone portion relative to an axis is indicated or shown accurately by the scale.

In addition, the frame of the present invention may further be provided with a structural element that is rotatable relative to another axis. The structural element engages the second arm holding the second bone portion. Further, the structural element includes a second scale to indicate rotation about the other axis which is not coincident with the axis of rotation of the first arm of the first clamp. Thus, the rotation of the first bone portion held by the first clamp and the second bone portion held by the second clamp may correspond to correction of internal/external rotational abnormalities and varus/valgus anatomical abnormalities, respectively. In essence, a compound osteotomy procedure may be accomplished by the frame of the present invention.

It may be apparent that a novel and useful osteotomy frame has been described.

It is therefore an object of the present invention to provide an osteotomy frame which permits the accurate rotation of one bone portion relative to another bone portion to a specified number of degrees in a straight forward manner.

Another object of the present invention is to provide an osteotomy frame which includes a mechanism controlling rotation of one bone portion relative to another bone portion in which said control is located apart from the center of rotation, i.e., the bone axis.

Another object of the present invention is to provide an osteotomy frame which permits rotation of a pair of bone portions relative to one another about multiple axes and is, thus, useful in compound osteotomy procedures.

A further object of the present invention is to provide an osteotomy frame having novel pivoting and rotational characteristics which may be employed with conventional saw guides.

A further object of the present invention is to provide an osteotomy frame which allows a single person to accomplish osteotomy procedures.

The invention possess other objects and advantages especially as concerns particular characteristics and features thereof which will become apparent as the specification continues.

Figure 1:
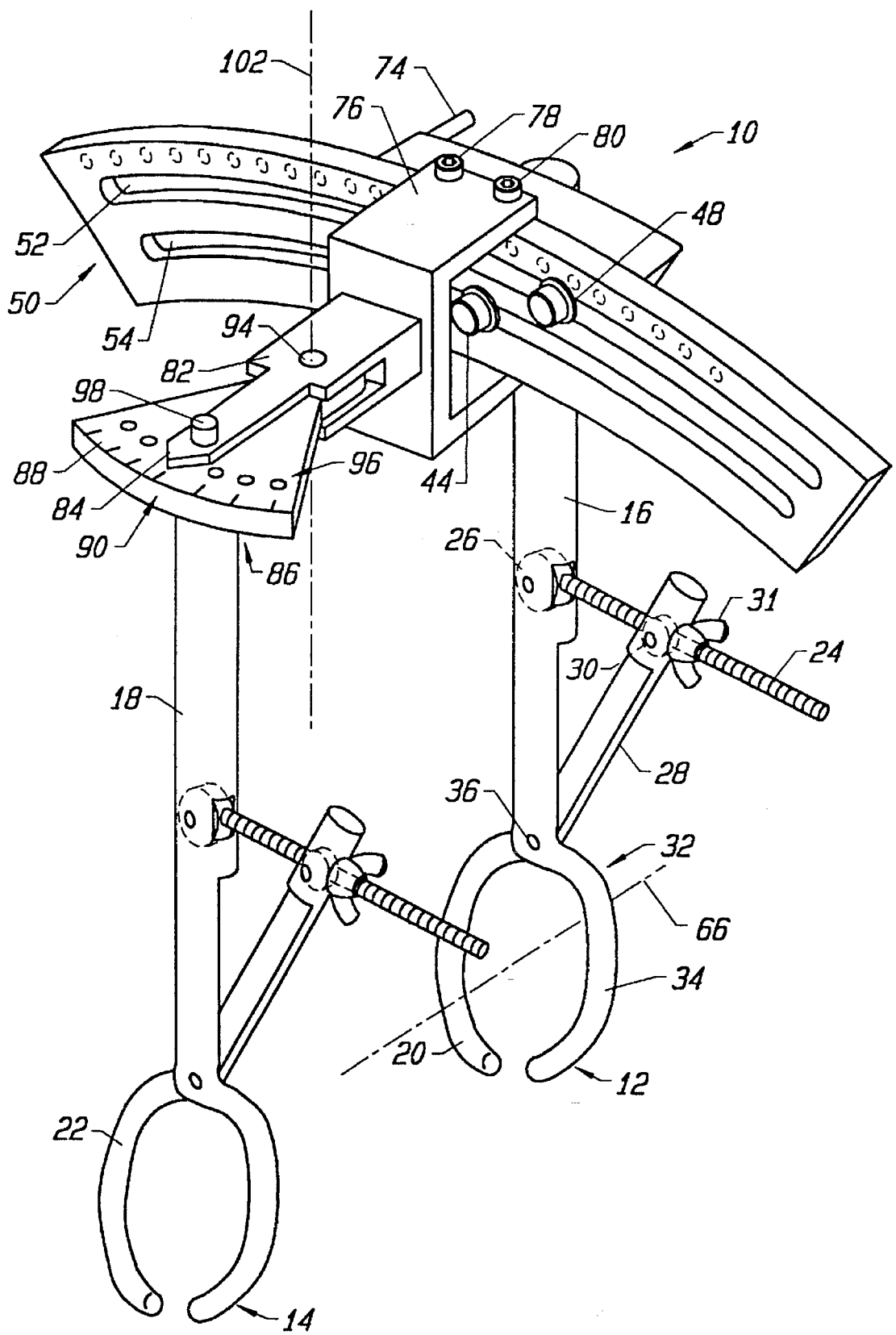
FIG. 1 is a top, rear, left side isometric view of the frame of the present invention in its entirety.

The invention possesses other objects and advantages especially as concerns particular characteristics and features thereof which will become apparent as the specification continues.

DETAILED DESCRIPTION OF THE PREFERRED EMBODIMENTS

Various aspects of the present invention will evolve from the following detailed description of the preferred embodiments which should be referenced to the hereinabove described drawings.

The invention as a whole is shown in the drawings by reference character 10. Osteotomy frame 10, FIG. 1, includes as two of its elements a first clamp 12 and second clamp 14. Clamps 12 and 14 are similarly constructed in that clamps 12 and 14 include arms 16 and 18 and movable jaw portions 20 and 22, respectively. In addition, with respect to exemplary clamp 12, an elongated threaded rod 24 terminates in a pivoting disk 26 within hollowed arm 16. Movable jaw 20 terminates in a hollowed elongated rod 28, which also contains a pivoting disk 30, threaded rod 24 passes through disk 30. Wing nut 31 threadingly engages elongated threaded rod 24, which in turn opens and closes grasping member 32 consisting of movable jaw 20 and stationary jaw 34 of clamp arm 16. Pivot pin 36 permits the rotation of movable jaw 20 relative to stationary jaw 34. Clamp 14 is similarly constructed.

Figure 3:
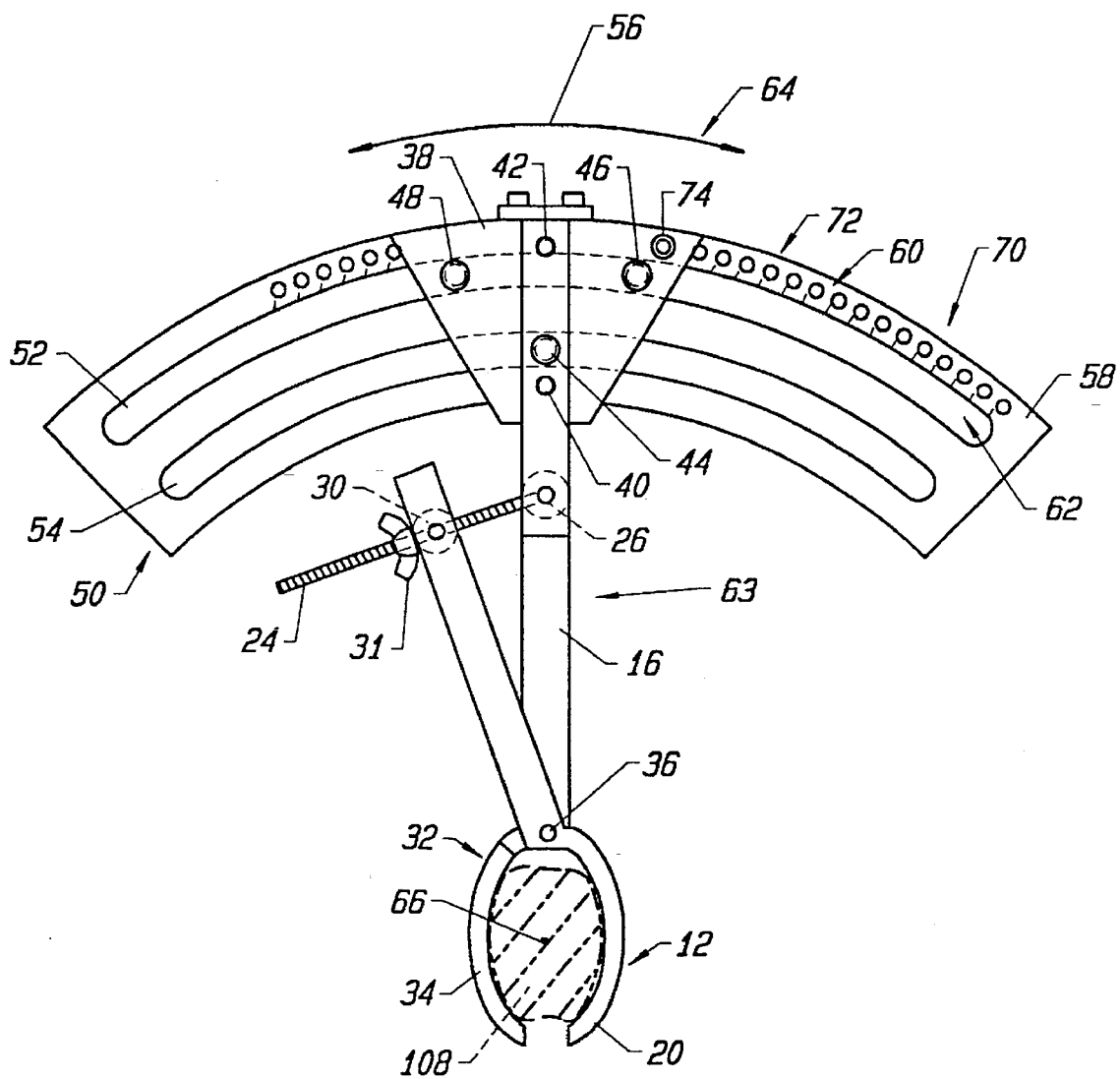
FIG. 3 is a front elevational view of the osteotomy frame of the present invention taken along line 3—3 of FIG. 2.

With reference to FIGS. 1 and 3, it may be observed that arms 16 extends to a trapezoidal-shape movable structure or gliding plate 38. Rivets 40 and 42 hold arm 16 to gliding plate 38 in rigid fashion. Gliding plate 38 includes cams 44, 46, and 48 which extend outwardly therefrom. Arcuate member 50 includes a pair of cams or slots 52 and 54. Cam followers 46 and 48 ride within slot 52 and cam follower 44 rides within slot 54. Thus, gliding plate 38 is guided along an arcuate path, directional arrow 56, either to the left or to the right as depicted on FIG. 3. Consequently, arcuate member 50, gliding plate 38, arms 16, and grasping member 32 comprise as pivoting means 68 for arm 16 of clamp 12 relative to axis 66. Surface 58 of arcuate member 50 includes a scale 60 comprising of plurality of slanted lines 62 of spaced configuration. Thus, edge 64 of gliding plate 38 is alignable with any of the plurality of slanted lines 62 to indicate the rotation of arm 16 about axis 66 passing through the center portion of grasping member 32, FIGS. 3 and 6. Numbers or other indicia may be marked next to slanted lines 62, as desired. Thus, it should be realized that scale 60 indicating such pivoting or rotation may take other forms such as a number scale, a window and glide plate 38, and the like.

Stop means 70 is also illustrated in FIG. 3 for fixing rotation of arm 16 relative to axis 66. Stop means is constructed, in the preferred embodiment, as a multiplicity of consecutive openings or recesses 72 into surface 58 of arcuate member 50. Movable pin 74 engages glide portion 38 and fits into any of the plurality of recesses 72. Pin 74 may be spring loaded in this regard to urge the same into the recesses 72. Thus, glide plate 38 may be fixed in its movement relative to arcuate member 50 according to stop means 70.

Figure 4:
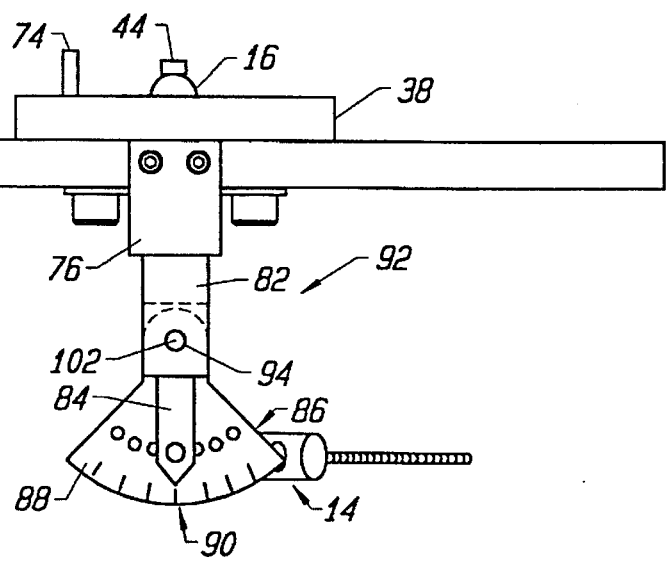
FIG. 4 is a top plan view of the osteotomy frame of the present invention taken along line 4—4 of FIG. 2.

Turning again to FIG. 1, arcuate member 50 connects to a C-bracket 76 by the use of set screws 78 and 80. A yolk shaped body 82 extends from C-bracket 76 and includes a pointer flange 84. Structural element 86 includes a surface 88 having a scale 90 thereupon, FIGS. 1 and 4. Second pivoting means 92 permits the rotation of structural member 86 relative to body 82 and C-bracket 76. Pivot pin 94 engages yolk body 82 and structural element 86 in this regard.

A plurality of recesses 96 at surface 88 of structural element 86 interacts with pin 98 through pointer flange 84. Consequently, stop pin 98 and plurality of recesses 96 serve as second stop means 100 to fix the rotation of structural element 86 relative to yolk body 82. Arm 18 and clamp 14 are fixedly connected to structural element 86. Thus, clamp 14 is rotatable relative to axis 102 which passes directly through pivot pin 94. Directional arrow 104, FIG. 5 indicates such rotation of clamp 14.

Figure 2:
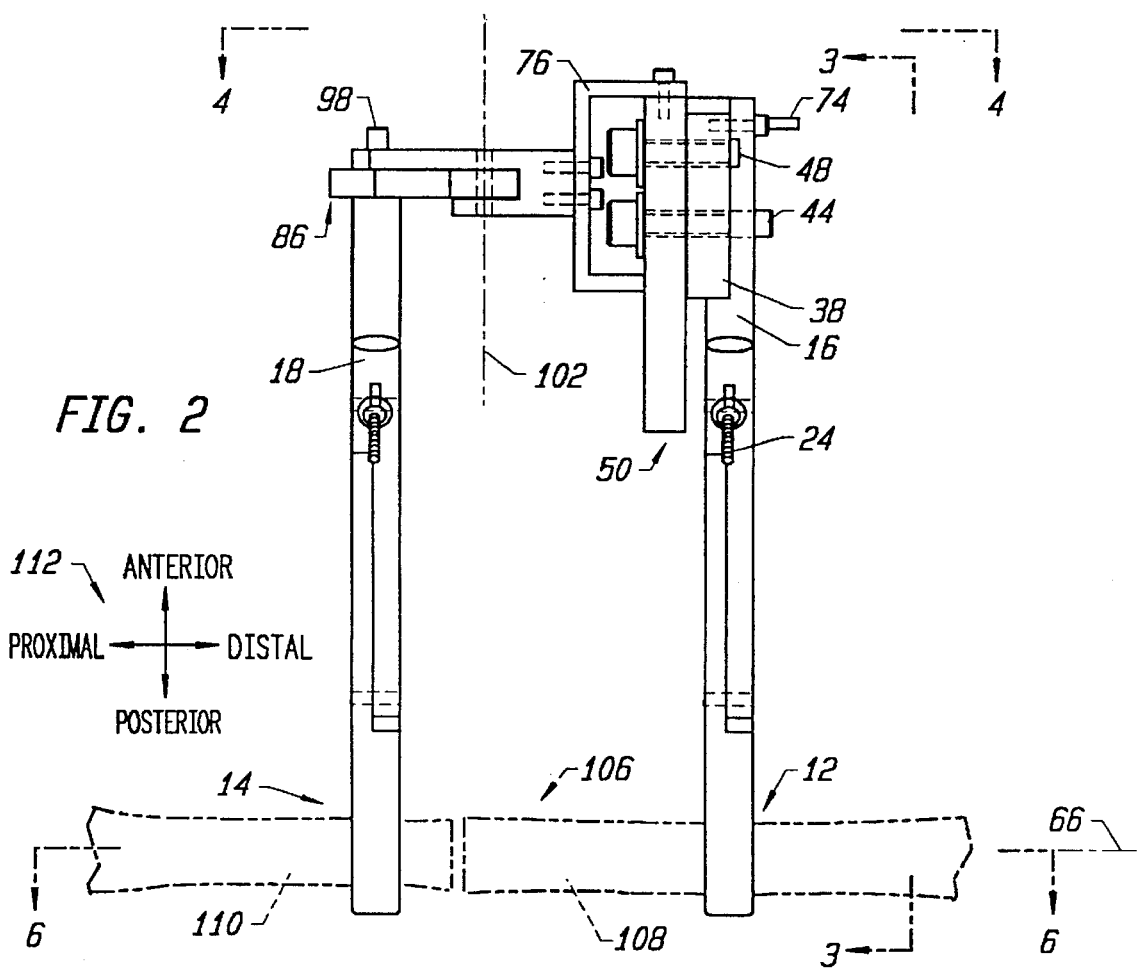
FIG. 2 is a left, side elevational view of the osteotomy frame of the present invention clamped to a pair of bone portions.
Figures 5, 6:
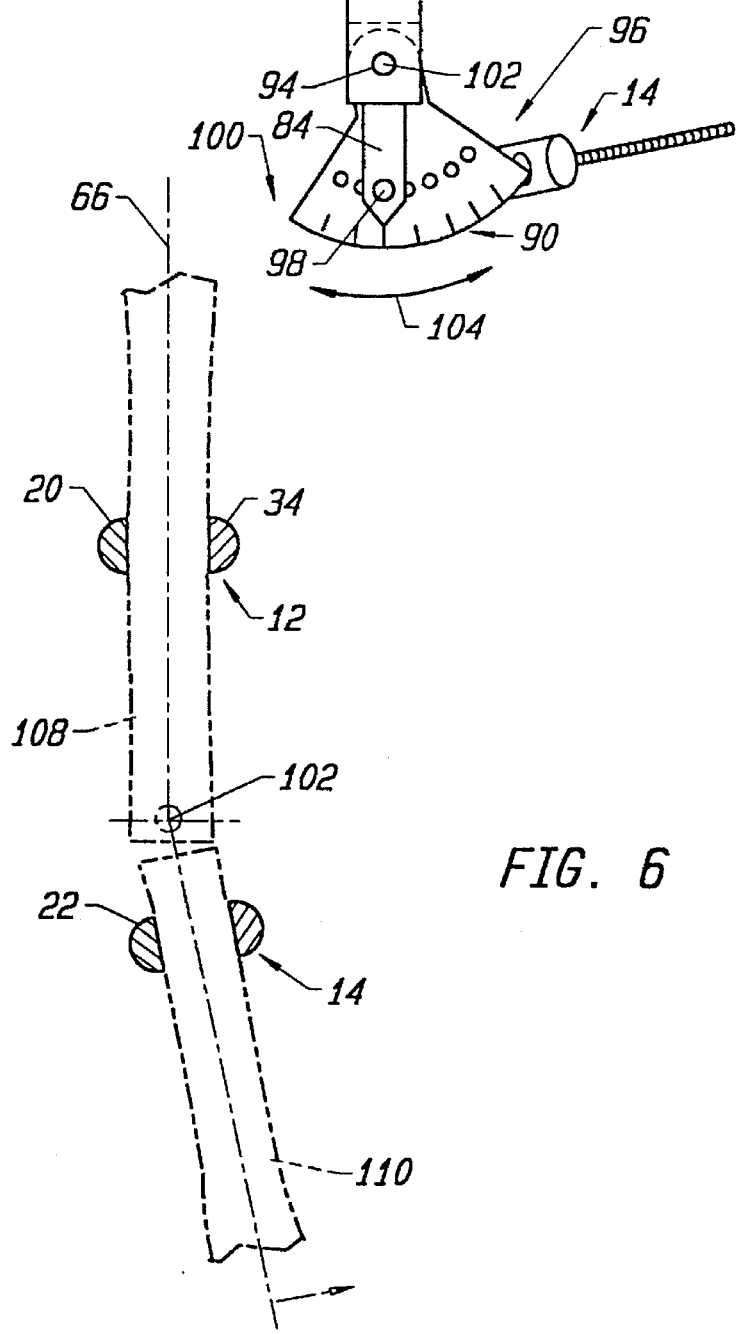
FIG. 5 is a top plan view of the osteotomy frame of the present invention showing the rotation of the second clamp to correct for varus/valgus abnormalities in an osteotomy procedure.
FIG. 6 is a top plan view of a pair of bone portions held by the pair of clamps of the osteotomy frame of the present invention indicating the axis of rotation of the two bone portions.

In operation, bone 106, shown in phantom on FIGS. 2, 3, and 6 is severed into bone portions 108 and 110 by a conventional saw guide, not shown. Clamp 12 is placed around bone portion 108 and tightened by wing nut 31 as shown in FIG. 3. Clamp 14 is similarly tightened about bone portion 110. Glide plate 38 is then moved along arcuate member 50 to rotate clamp 12 about axis 66 to a desired degree. Scale 60 indicates such rotation. Stop pin 74 is inserted in any of the plurality of recesses 72 of arcuate member 50 to hold clamp 12 in a certain position of rotation about axis 66. Such correction in an osteotomy procedure is normally referred to as the internal/external rotational abnormality correction. Again, referring to FIG. 2, index 112 depicts the general orientation of the bone relative to the patient. Clamp 14 is then rotated about axis 102 and fixed in a position by set pin 98 which engages any one of the plurality of recesses 96 of moveable structural element 86. With reference to FIG. 6, such movement of bone portion 110 relative to bone portion 108 is depicted about axis 102. Such correction in osteotomy procedure is referred to as the varus/valgus abnormality correction. Thus, a compound osteotomy procedure may be accomplished with frame 10. Following rotation about axes 66 and 102, bone portions 108 and 110 are fixated. It has been found that the frame of the present invention provides for a very accurate and efficient rotating of bone portions in osteotomy or compound osteotomy procedure. In other words, either clamp 12 or 14 may be rotated alone to correct a bone deformity about either axis 66 or axis 102.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An osteotomy frame for aligning first and second bone portions comprising:

a first clamp for holding the first bone portion and a second clamp for holding the second bone portion, said first and second clamps comprising lockable jaw portions for locking said clamps to said first and second bone portions;

an arm connected to said first clamp;

pivoting means for rotating said arm connected to said first clamp relative to a longitudinal axis of said first bone portion; and a scale, said arm interacting with said scale to show a value of rotation about said axis.

2. The frame of claim 1 in which said pivoting means for rotating said arm comprises an arcuate member having a track and movable structure capable of riding said track, said arm being connected to said arcuate member.

3. The frame of claim 2 in which arcuate member includes a portion for placement of said scale.

4. The frame of claim 2 in which said track comprises an arcuate groove and said movable structure includes a follower for riding said arcuate groove.

5. The frame of claim 2 in which said track comprises a pair of arcuate grooves and said movable structure includes a pair of cams, each riding one of said pair arcuate grooves.

6. The frame of claim 1 in which said scale is a first scale, said pivoting means is a first pivoting means and said axis is a first axis and said frame additionally comprises a second scale, said second scale being linked to said second clamp, and second pivoting means indicating rotation of said second clamp relative to a second axis.

7. The frame of claim 6 in which said second scale includes a structural element having a surface with indicia, and said second pivoting means including a body, said structural element being rotatable relative to said body on said second axis.

8. The frame of claim 7 in which said body further includes a flange extending to the vicinity of said surface of said structural element.

9. The frame of claim 8 which further comprises a plurality of indents on said surface of said structural element and said flange includes a stop for engaging any of said plurality of indents.

10. The frame of claim 9 in which said first axis is not coincident with said second axis.

11. The frame of claim 6 in which said first axis is not coincident with said second axis.

12. The frame of claim 11 in which said body further includes a flange extending to the vicinity of said surface of said structural element and said second scale.

13. The frame of claim 12 which further comprises a plurality of indents on said surface of said structural element and said flange includes a stop for engaging any of said plurality of indents.

* * * * *